United States Patent
Saijoh et al.

(10) Patent No.: US 9,304,105 B2
(45) Date of Patent: Apr. 5, 2016

(54) CONTROL DEVICE FOR OXYGEN CONCENTRATION SENSOR

(71) Applicant: DENSO CORPORATION, Kariya, Aichi-pref. (JP)

(72) Inventors: Masaki Saijoh, Kariya (JP); Takamasa Oguri, Toyoake (JP); Kouji Morishita, Kariya (JP)

(73) Assignee: DENSO CORPORATION, Kariya (JP)

( * ) Notice: Subject to any disclaimer, the term of this patent is extended or adjusted under 35 U.S.C. 154(b) by 136 days.

(21) Appl. No.: 14/138,433

(22) Filed: Dec. 23, 2013

(65) Prior Publication Data

US 2014/0191773 A1 Jul. 10, 2014

(30) Foreign Application Priority Data

Jan. 10, 2013 (JP) .................................... 2013-2605

(51) Int. Cl.
*G01R 27/08* (2006.01)
*G01N 27/417* (2006.01)

(52) U.S. Cl.
CPC .................................. *G01N 27/4175* (2013.01)

(58) Field of Classification Search
CPC ..... G01N 27/26; G01N 27/41; G01N 27/401; G01N 27/4175; G01R 1/07342; G01R 35/00; G11B 5/3166; G11B 5/3169
USPC ............. 73/114.69, 114.71–114.73; 204/424, 204/427, 406; 324/705, 378–402
See application file for complete search history.

(56) References Cited

U.S. PATENT DOCUMENTS

| 5,935,400 | A  | * | 8/1999  | Takami et al. ................ 204/425 |
| 6,073,083 | A  | * | 6/2000  | Schnaibel et al. .............. 702/65 |
| 6,084,418 | A  | * | 7/2000  | Takami et al. ................ 324/717 |
| 6,468,478 | B1 | * | 10/2002 | Honda ............................ 422/98 |
| 8,961,761 | B2 | * | 2/2015  | Maeda .......................... 204/424 |
| 2004/0099041 | A1 | * | 5/2004 | Hattori .......................... 73/1.06 |
| 2005/0000810 | A1 | * | 1/2005 | Tashiro et al. ................ 204/424 |
| 2012/0119763 | A1 | * | 5/2012 | Adkins .................. G01R 27/14 324/705 |

FOREIGN PATENT DOCUMENTS

| JP | 2005-140642 A | 6/2005 |
| JP | 2006-250695 A | 9/2006 |
| JP | 2006-329924 A | 12/2006 |

* cited by examiner

*Primary Examiner* — Arleen M Vazquez
*Assistant Examiner* — Steven Yeninas
(74) *Attorney, Agent, or Firm* — Posz Law Group, PLC (57) ABSTRACT

A control device for controlling an oxygen concentration sensor includes: a voltage sweeping unit for applying a voltage to the sensor for a time interval during an impedance detection process; a pre-sweeping voltage memory for storing a terminal voltage of the sensor as an initial terminal voltage just before applying the voltage; an impedance detection unit for detecting an element impedance; a voltage returning unit for returning the terminal voltage to the initial terminal voltage after a predetermined time interval has elapsed; a monitoring unit for monitoring the terminal voltage after the voltage returning unit starts returning the terminal voltage; a determination unit for determining whether a monitored terminal voltage of the sensor reaches a stored terminal voltage in the memory; and a stop unit for stopping a returning operation of the voltage returning unit when the monitored terminal voltage reaches the stored terminal voltage.

2 Claims, 5 Drawing Sheets

CONTROL DEVICE FOR OXYGEN CONCENTRATION SENSOR

CROSS REFERENCE TO RELATED APPLICATION

This application is based on Japanese Patent Application No. 2013-2605 filed on Jan. 10, 2013, the disclosure of which is incorporated herein by reference.

TECHNICAL FIELD

The present disclosure relates to a control device for controlling an oxygen concentration sensor.

BACKGROUND

Conventionally, an oxygen concentration sensor is arranged in an exhaust pipe of an internal combustion engine. An ECU (i.e., electronic control unit) obtains information about an air fuel ratio in an exhaust gas (i.e., exhaust gas air/fuel ratio) based on a signal from the oxygen concentration sensor. These features are disclosed in JP-A-2004-340914 corresponding to US 2005/0000810. A control device for controlling the oxygen concentration sensor detects an element impedance of the oxygen concentration sensor by switching an applied voltage of the sensor from a standard voltage to a sweeping voltage while the ECU obtains the information relating to the exhaust gas air/fuel ratio. In JP-A-2004-340914, a discharging time of the applied voltage of the sensor is determined according to a map data (i.e., a two-dimensional map) of the discharging time, which is made with using a terminal voltage of the sensor before sweeping and a previous detection value of the impedance as variables.

An output signal from the sensor is utilized for an engine control. Accordingly, after the element impedance is detected, it is necessary to recover the applied voltage of the sensor to be the standard voltage. In a conventional method, it is necessary to adapt the map data of the discharging time at each chip set. Therefore, it takes much time to adapt the map data.

SUMMARY

It is an object of the present disclosure to provide a control device for controlling an oxygen concentration sensor. The control device detects an element impedance of the sensor while the control device obtains information about an exhaust gas air/fuel ratio based on an output voltage of the sensor, and immediately recovers a terminal voltage of the sensor to be a state before executing an element impedance detection process without adapting a map data.

According to a first aspect of the present disclosure, a control device for controlling an oxygen concentration sensor includes: a voltage sweeping unit for applying a voltage to the oxygen concentration sensor for a predetermined time interval during an impedance detection process, in which information about an exhaust gas air and fuel ratio is obtained according to an output voltage of the oxygen concentration sensor; a pre-sweeping voltage memory for storing a terminal voltage of the oxygen concentration sensor, which is referred as an initial terminal voltage, just before the voltage sweeping unit applies the voltage to the oxygen concentration sensor; an impedance detection unit for detecting an element impedance in accordance with the voltage applied by the voltage sweeping unit; a voltage returning unit for returning the terminal voltage of the oxygen concentration sensor to the initial terminal voltage after a predetermined time interval has elapsed since the voltage sweeping unit applies the voltage to the oxygen concentration sensor; a monitoring unit for monitoring the terminal voltage of the oxygen concentration sensor after the voltage returning unit starts returning the terminal voltage of the oxygen concentration sensor to the initial terminal voltage; a determination unit for determining whether a monitored terminal voltage of the oxygen concentration sensor reaches a stored terminal voltage in the pre-sweeping voltage memory; and a stop unit for stopping a returning operation of the voltage returning unit when the determination unit determines that the monitored terminal voltage reaches the stored terminal voltage.

In the above control device, the voltage sweeping unit applies the voltage to the oxygen concentration sensor for a predetermined time interval during an impedance detection process, in which information about an exhaust gas air and fuel ratio is obtained according to an output voltage of the oxygen concentration sensor. The pre-sweeping voltage memory stores a terminal voltage of the oxygen concentration sensor just before the voltage sweeping unit applies the voltage to the oxygen concentration sensor. The impedance detection unit detects an element impedance by measuring the current flowing in accordance with the voltage applied by the voltage sweeping unit. Thus, while the information about the exhaust gas air and fuel ratio is obtained, the element impedance of the sensor is detected.

Further, the voltage returning unit controls the terminal voltage of the oxygen concentration sensor to return to the initial terminal voltage after a predetermined time interval has elapsed. The monitoring unit monitors the terminal voltage of the oxygen concentration sensor after the voltage returning unit starts returning the terminal voltage of the oxygen concentration sensor to the initial terminal voltage until the terminal voltage of the oxygen concentration sensor reaches the initial terminal voltage. The determination unit determines whether a monitored terminal voltage of the oxygen concentration sensor reaches a stored terminal voltage in the pre-sweeping voltage memory. The stop unit stops a returning operation of the voltage returning unit when the determination unit determines that the monitored terminal voltage reaches the stored terminal voltage. Thus, the terminal voltage of the sensor is stabilized. Accordingly, without adapting and generating the map data, the terminal voltage of the sensor is recovered to the initial terminal voltage, which is the initial state before the element impedance detection process, quickly.

According to a second aspect of the present disclosure, a control device for controlling an oxygen concentration sensor includes: a voltage sweeping unit for applying a voltage to the oxygen concentration sensor for a predetermined time interval during an impedance detection process, in which information about an exhaust gas air and fuel ratio is obtained according to an output voltage of the oxygen concentration sensor; a pre-sweeping voltage memory for storing a terminal voltage of the oxygen concentration sensor, which is referred as an initial terminal voltage, just before the voltage sweeping unit applies the voltage to the oxygen concentration sensor; an impedance detection unit for detecting an element impedance in accordance with the voltage applied by the voltage sweeping unit; a voltage returning unit for returning the terminal voltage of the oxygen concentration sensor to the initial terminal voltage after a predetermined time interval has elapsed since the voltage sweeping unit applies the voltage to the oxygen concentration sensor; a monitoring unit for monitoring the terminal voltage of the oxygen concentration sensor after the voltage returning unit starts returning the terminal voltage of the oxygen concentration sensor to the initial terminal voltage; a determination unit for determining whether a monitored terminal voltage of the oxygen concentration sensor reaches a certain voltage, which is calculated by adding an offset voltage to a stored terminal voltage in the pre-sweeping voltage memory, or by subtracting the offset voltage from the stored terminal voltage; and a stop unit for stopping a returning operation of the voltage returning unit when the determination unit determines that the monitored terminal voltage reaches the certain terminal voltage.

In the above control device, while the information about the exhaust gas air and fuel ratio is obtained, the element impedance of the sensor is detected. Further, the determination unit determines whether a monitored terminal voltage of the oxygen concentration sensor reaches a certain voltage, which is calculated by adding an offset voltage to a stored terminal voltage in the pre-sweeping voltage memory, or by subtracting the offset voltage from the stored terminal voltage. The stop unit stops a returning operation of the voltage returning unit when the determination unit determines that the monitored terminal voltage reaches the certain terminal voltage. Thus, the terminal voltage of the sensor is stabilized. Accordingly, without adapting and generating the map data, the terminal voltage of the sensor is recovered to the initial terminal voltage, which is the initial state before the element impedance detection process, quickly.

BRIEF DESCRIPTION OF THE DRAWINGS

The above and other objects, features and advantages of the present disclosure will become more apparent from the following detailed description made with reference to the accompanying drawings. In the drawings.

DETAILED DESCRIPTION

First Embodiment

Figure 2:
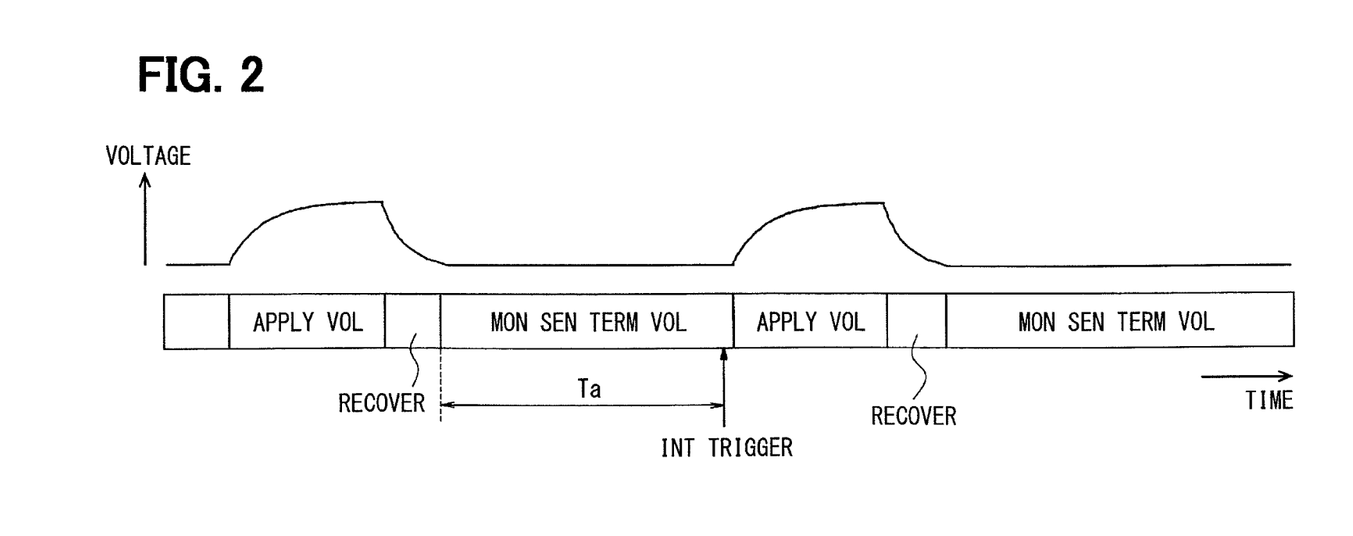
FIG. 2 is a timing chart showing a relationship between a terminal voltage of an oxygen concentration sensor and time.
Figure 3:
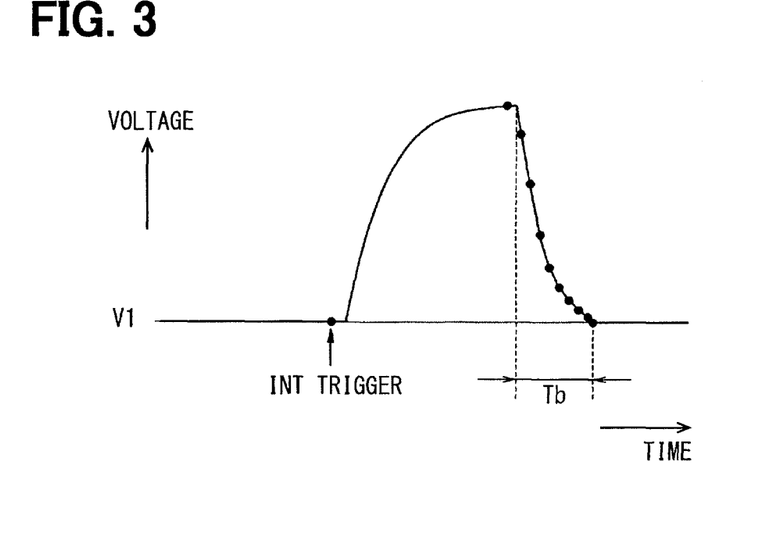
FIG. 3 is a timing chart showing a sampling voltage and a sampling timing.

A control device for controlling an oxygen concentration sensor according to a first embodiment will be explained as follows with reference to FIGS. 1 to 3.

Figure 1:
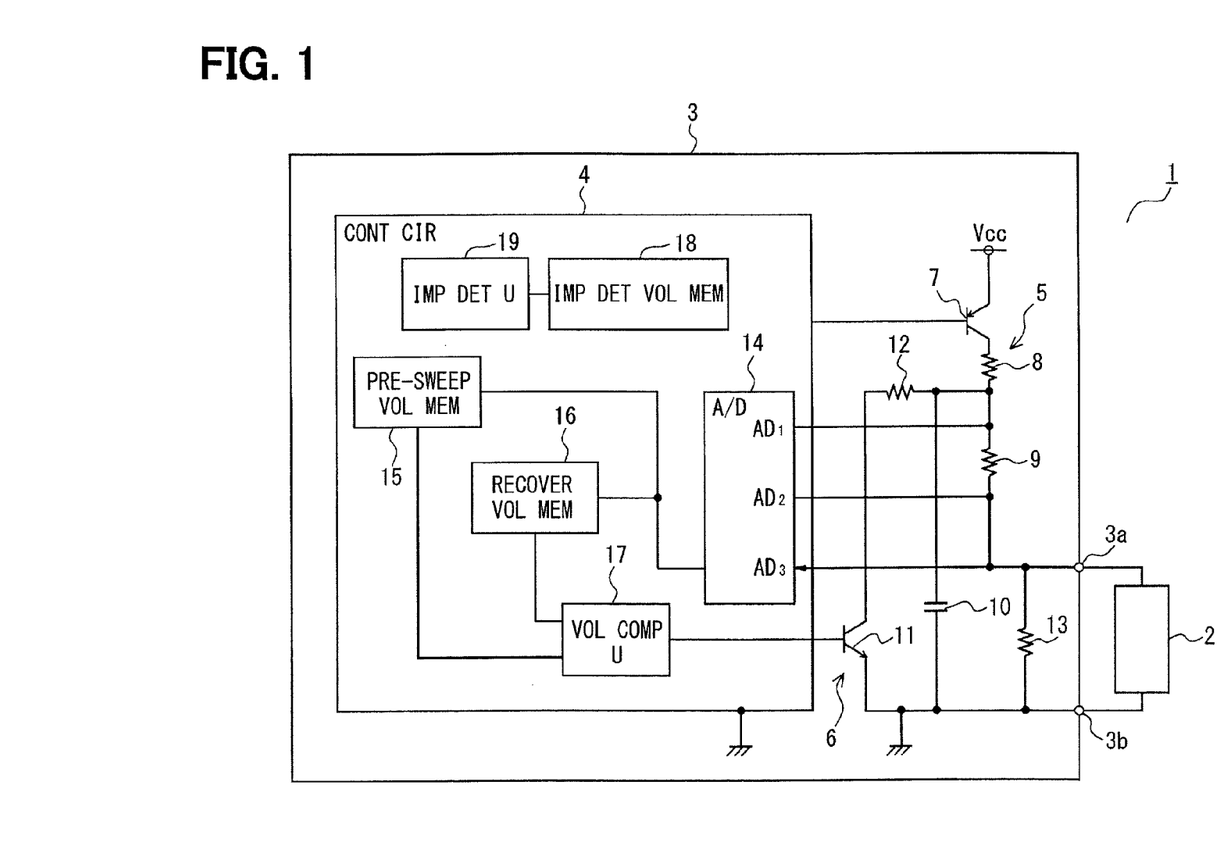
FIG. 1 is a circuit diagram showing a system according to a first embodiment.

A system 1 shown in FIG. 1 includes the oxygen concentration sensor 2 and a control device 3 as an electronic control unit (i.e., ECU). The sensor 2 is arranged in an exhaust pipe of an internal combustion engine (not shown). The sensor 2 is equivalent to a circuit having a resistance component impedance and an electro motive force component (and a small amount of a capacitance component), which are connected in series with each other. The sensor 2 is an electro motive force type sensor for outputting a voltage corresponding to one of a rich state and a lean state of the exhaust gas air/fuel ratio so as to determine whether the exhaust gas air/fuel ratio is in the rich state or the lean state.

In the present embodiment, the control device 3 is connected to the sensor 2 such that a terminal 3a of the device 3 is in a high voltage side, and a terminal 3b is in a low voltage side. A voltage generated between the terminals 3a, 3b is detected so that the control device 3 determines whether the exhaust gas air/fuel ratio is in the rich state or the lean state.

The control device 3 has a function for detecting an element impedance Rs of the sensor 2 periodically while the control device 3 determines whether the exhaust gas air/fuel ratio is in the rich state or the lean state. Accordingly, the control device 3 has a function for obtaining information about the exhaust gas air/fuel ratio according to the terminal voltage of the sensor 2 and a function for detecting the element impedance Rs of the sensor 2.

An internal construction of the control device 3 will be explained as follows. The control device 3 includes a control circuit 4 having a micro processor with a CPU (central processing unit) and a memory, a sweeping voltage applying circuit 5 for applying a voltage to the sensor 2, and a recover circuit 6 for discharging the voltage applied to a terminal of the sensor. The sweeping voltage applying circuit 5 and the recover circuit 6 are discrete elements, respectively.

The sweeping voltage applying circuit 5 includes, for example, a switch 7 having a PNP transistor, resistors 8, 9 and a capacitor 10. When the control circuit 4 controls the switch 7 to turn on, the capacitor 10 is energized, so that the circuit 5 applies the voltage to the sensor 2.

The recover circuit 6 includes, for example, a switch 11 having a NPN transistor, resistors 9, 12, 13 and a capacitor 10. When the control circuit 4 controls the switch 11 to turn on, the circuit 6 discharges an accumulated electric charge in the sensor 2 and the capacitor 10, so that the circuit 6 reduces a voltage between terminals of the sensor 2.

A connection line in the system 1 according to the present embodiment will be explained as follows. The connection line in the system 1 may be made in a different way as long as the voltage is applied to the terminals of the sensor 2 and an inter terminal voltage of the sensor 2 is discharged within an impedance detection process period. In the present embodiment, the switch 7 and the resistors 8, 9, 13 are connected in series with each other between a supply terminal of a power source voltage Vcc and a ground terminal. The capacitor 10 is connected in parallel to a series circuit of the resistors 9, 13. Further, the resistor 12 and the switch 11 are connected in series with each other between terminals of the capacitor 10. A control output terminal of the control circuit 4 is connected to both of control terminals of the switches 7, 11.

The control circuit 4 includes an A/D converting unit 14. The A/D converting unit 14 converts each of a voltage at a common connection node between the resistors 8, 9, a voltage at a common connection node between the resistors 9, 13, and an inter-terminal voltage of the sensor 2 from an analog voltage to a digital voltage so that an A/D conversion is performed.

A register is arranged as a memory in the control circuit 4. The memory is provided by a pre-sweeping voltage memory 15 and a recover voltage memory 16. The pre-sweeping voltage memory 15 stores an A/D value of the inter-terminal voltage of the sensor 2 as an initial value when an interruption trigger for starting to execute the detection process of the element impedance Rs occurs. Specifically, the pre-sweeping voltage memory 15 stores the inter-terminal voltage of the sensor 2 as a digital value just before the sweeping process for applying the voltage is performed during the element impedance detection process period.

The recover voltage memory 16 stores multiple A/D values of the inter-terminal voltage of the sensor 2 while the control circuit 4 controls the recover circuit 6 to recover the inter-terminal voltage of the sensor 2 to be the initial value. For example, the recover voltage memory 16 stores multiple values of the inter-terminal voltage of the sensor 2 during the recover process period.

A voltage comparison unit 17 is arranged in the control circuit 4. The voltage comparison unit 17 compares a value of the pre-sweeping voltage memory 15 with a value of the recover voltage memory 16. The voltage comparison unit 17 controls the switch 11 to turn off when a stored value in the recover voltage memory 16 reaches the value of the pre-sweeping voltage memory 15 during the recover process, so that the driving operation of the recover circuit 6 is stopped. Here, the trigger is a fact that the stored value in the recover voltage memory 16 reaches the value of the pre-sweeping voltage memory 15 during the recover process.

In the present embodiment, the function of the voltage comparison unit 17 is realized by the execution of the software program stored in the memory with the CPU in the control circuit 4. Various functional units for controlling the engine, for example, in addition to the units 14-17 are mounted.

While the engine is running, temperature around the sensor 2 varies. The element impedance Rs of the sensor 2 has temperature dependency. When the temperature of the sensor increases, the element impedance Rs becomes small. In order to control the sensor 2 with the control circuit 4 appropriately, the peripheral temperature of the sensor 2 is controlled to be predetermined active temperature so that the element impedance Rs is controlled appropriately. Accordingly, the element impedance Rs is accurately detected, and the feed back control of the element impedance Rs is performed precisely. Further, when the control circuit 4 detects the element impedance Rs, the control circuit 4 can diagnose the error of the sensor 2.

Thus, the control circuit 4 detects the element impedance Rs periodically according to the information of the inter-terminal voltage of the sensor 2 while the determination about the rich state and the lean state of the exhaust gas air/fuel ratio. In order to detect the element impedance Rs, the control circuit 4 applies a voltage in addition to the initial value (i.e., the inter-terminal voltage just before the impedance detection process) for predetermined time interval. After the predetermined time interval has elapsed, the control circuit 4 obtains the element impedance Rs in accordance with the A/D value of the A/D converting unit 14.

The control circuit 4 controls the inter-terminal voltage of the sensor 2 to return to the initial value V1 (i.e., the voltage before sweeping the inter-terminal voltage) after the control circuit 4 applies the additional voltage to the sensor 2. When the control circuit 4 returns the inter-terminal voltage to the initial value quickly, the determination of the rich state and the lean state is restarted using the sensor signal of the sensor 2 quickly.

In the present embodiment, the impedance detection process and the voltage after the impedance detection process provide the characteristics of the present embodiment. Accordingly, these processes will be explained as follows. FIG. 2 shows a timing chart of a time variation of the inter-terminal voltage of the sensor 2. FIG. 3 shows the sampling voltage during the impedance detection process. In the lean/rich determination period Ta shown in FIG. 2, the switches 7, 11 are in the off-state, so that the terminals of the sensor 2 are opened. The control circuit 4 converts the inter-terminal voltage of the sensor 2 from an analog value to a digital value at every four milliseconds in the lean/rich determination period Ta, so that the converted inter-terminal voltage is held and sampled (i.e., a sample holding process of the inter-terminal voltage is performed). Thus, the control device 2 determines where the control circuit 4 determines based on the converted inter-terminal voltage whether the exhaust gas air/fuel ratio is in the lean state or the rich state. The lean/rich determination period Ta is set to 128 milliseconds, for example.

When the control circuit 4 generates the interruption trigger for the impedance detection process at the end of the lean/rich determination period Ta, the inter-terminal voltage of the sensor 2 is sampled and held, and the sampled and held voltage value is stored in the pre-sweeping voltage memory 15.

The control circuit 4 controls the switch 7 to turn on, so that the control circuit 4 forcibly energizes the capacitor 10 and the sensor 2 in order to apply the voltage to the sensor 2 for the predetermined time interval. The predetermined time interval is a predetermined fixed time interval, which is set to be much shorter than the lean/rich determination period Ta. For example, the predetermined fixed time interval is a few hundreds microseconds such as 155 microseconds. In this case, the sweeping voltage applying circuit 5 increases the inter-terminal voltage of the sensor 2 with a time constant corresponding to the real part impedance of the element impedance Rs.

The control circuit 4 generates the voltage applying completion trigger just before the predetermined time interval has elapsed, the control circuit 4 performs the A/D conversion of two channel parts of the analog voltage value with the A/D converting unit 14. Then, the control circuit 4 samples and holds the converted voltage, and controls an impedance detection voltage memory 18 to store the converted voltage. The impedance detection unit 19 in the control circuit 4 calculates the element impedance Rs of the sensor 2 with using each terminal voltage stored in the impedance detection voltage memory 18.

The control circuit 4 controls the switch 11 to turn on at the same time when the control circuit 4 controls the switch 7 to turn off after the predetermined time interval has elapsed. The control circuit 4 holds the A/D converted value, which is prepared by the A/D converting unit 14, and then, the control circuit 4 controls the recover voltage memory 16 to store the A/D converted value sequentially. The period for storing the terminal voltage of the sensor 2 in the recover voltage memory 16 is set to be a few microseconds such as 5 microseconds. Thus, the recover voltage memory 16 can store multiple points from the switch 11 turns on until the inter-terminal voltage of the sensor 2 returns to the initial value V1. That is, the memory 16 stores multiple A/D converted values in the period Tb, which are shown as black circles in FIG. 3.

When the recover voltage memory 16 stores multiple converted voltage values, the voltage comparison unit 17 compares newly stored voltage values with the voltage stored in the pre-sweeping voltage memory 15 in order. When the voltage comparison unit 17 determines that the newly stored voltage value reaches the voltage (i.e., the initial value V1) stored in the pre-sweeping voltage memory 15, the control circuit 4 controls the switch 11 to turn off. Thus, the output voltage of the sensor 2 returns to the voltage before sweeping, so that the output voltage of the sensor 2 is stabilized.

After the control circuit 4 confirms that the terminals in the sensor 2 are opened, the control circuit 4 coverts the sensor signal from the sensor 2 from an analog signal to a digital signal. Thus, the control circuit 4 restarts the lean/rich determination process in accordance with the exhaust gas air/fuel ratio.

In the present embodiment, the control circuit 4 obtains the information relating to the exhaust gas air/fuel ratio based on the output voltage of the sensor 2. When the control circuit 4 generates the interruption trigger of the impedance detection process asynchronously, the control circuit 4 stores the inter-terminal voltage of the sensor 2 (i.e., the initial value V1) in the pre-sweeping voltage memory 15, and then, the control circuit 4 applies the voltage in addition to the initial value to the sensor for the predetermined time interval. Then, the control circuit 4 detects the impedance. Accordingly, the control device 3 detects the element impedance Rs of the sensor 2 while the control device 3 obtains the information about the exhaust gas air/fuel ratio.

When the control circuit 4 controls the switch 11 to turn on so that the control circuit 4 controls the sensor 2 to sweep back, the inter-terminal voltage of the sensor 2 is monitored by the A/D converting unit 14 so as to detect multiple points while the inter-terminal voltage of the sensor 2 is converted from an analog value to a digital value, and swept back to the initial value V1. The voltage comparison unit 17 controls the switch 11 to turn off so that the control circuit 4 stabilizes the inter-terminal voltage of the sensor 2 when the inter-terminal voltage of the sensor 2 returns to the initial value V1. Thus, without adapting and generating the map data, the inter-terminal voltage of the sensor 2 is recovered to the initial value V1, which is the initial state before the element impedance detection process, quickly.

Second Embodiment

Figure 4:
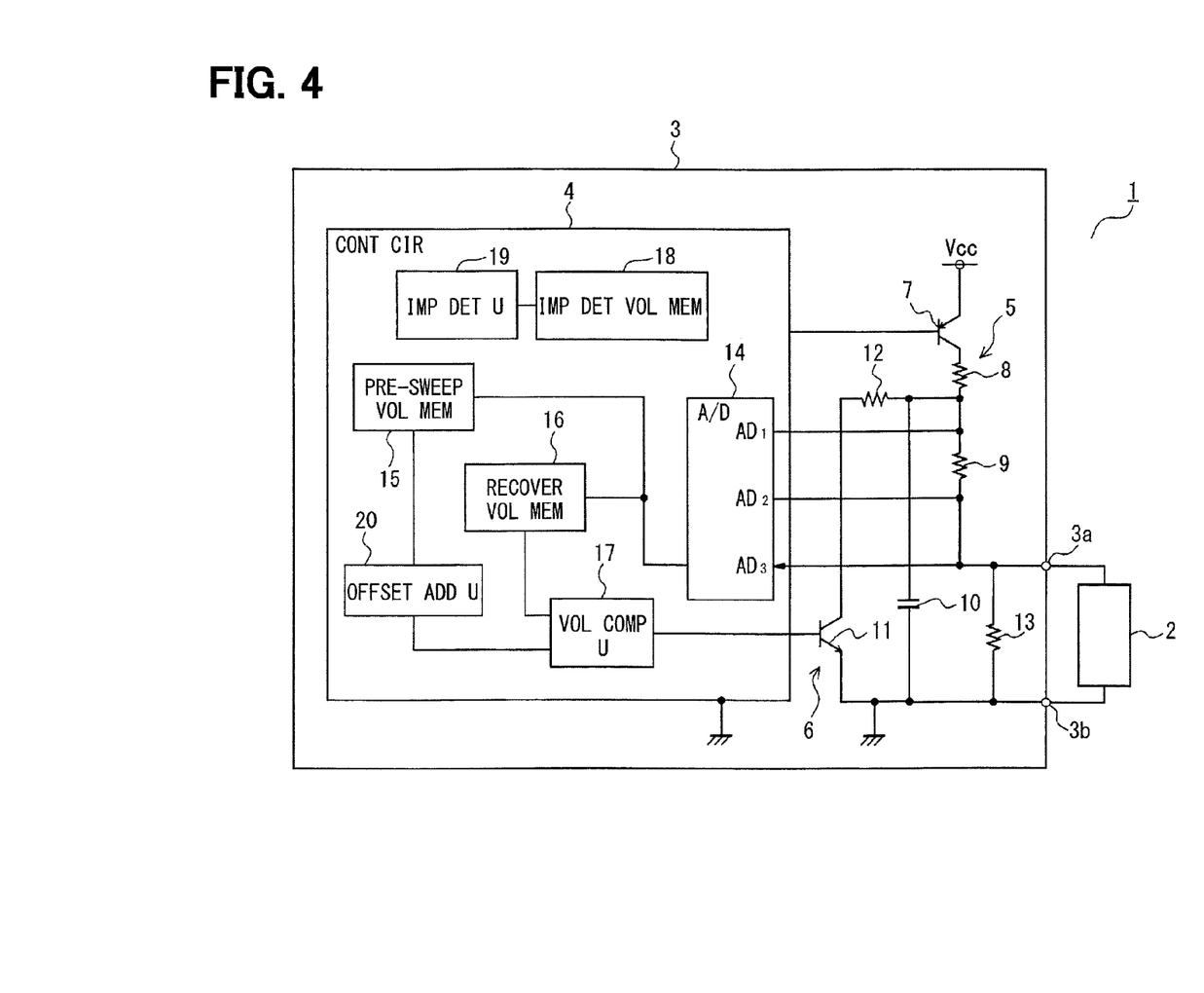
FIG. 4 is a circuit diagram showing a system according to a second embodiment.
Figure 5:
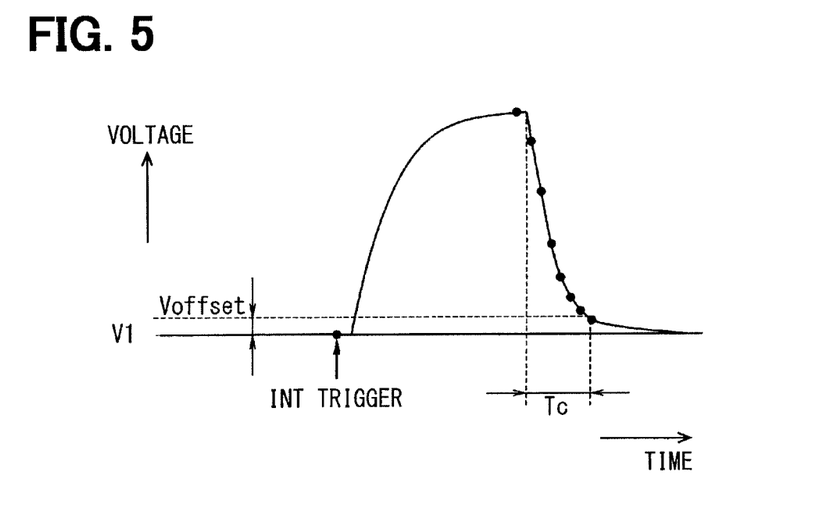
FIG. 5 is a timing chart showing a sampling voltage and a sampling timing according to the second embodiment.

FIGS. 4 and 5 show a system 1 according to a second embodiment. In the second embodiment, the control device 3 determines whether the offset voltage reaches a voltage, which is prepared by adding to or subtracting from a predetermined voltage. When the control device 3 determines that the offset voltage reaches the added or subtracted voltage, the control device 3 stops a sweeping back operation (i.e., return sweeping operation).

As shown in FIG. 4, an offset adding unit 20 is arranged on a latter step of the pre-sweeping voltage memory 15. The offset adding unit 20 is a block circuit for adding the offset voltage Voffset to a certain voltage. The CPU executes a software program so that the function of the offset adding unit 20 is provided.

The offset adding unit 20 adds the offset voltage Voffset to the voltage stored in the pre-sweeping voltage memory 15 in a plus direction, for example. The voltage comparison unit 17 compares an added voltage, which is prepared by adding the offset voltage Voffset with the offset adding unit 20, with the stored voltage in the recover voltage memory 16. The control device 3 stops an driving operation of the recover circuit 6 by controlling the switch 11 to turn off when the inter-terminal voltage of the sensor 2 reaches (or falls below) the added voltage, which is prepared by adding the offset voltage Voffset to the initial state (i.e., the initial value V1), during the recover sweeping process (i.e., return sweeping process). Here, the trigger is a fact that the inter-terminal voltage of the sensor 2 reaches the added voltage, and the recover sweeping process period Tc in FIG. 5 ends when the trigger is generated.

Thus, as shown in FIG. 5, when the control circuit 4 determines that the inter-terminal voltage of the sensor 2 reaches the added voltage, which is prepared by adding the offset voltage Voffset to the initial voltage V1, while the recover sweeping process is executed, the control circuit 4 controls the switch 11 to turn off, so that the driving operation of the recover circuit 6 is stopped. Thus, the inter-terminal voltage of the sensor 2 is returned to a value nearly equal to the initial voltage V1 in the initial state. After that, the inter-terminal voltage of the sensor 2 is moderately reduced in accordance with the impedance in the sensor 2 so that the inter-terminal voltage asymptotically approaches the initial voltage V1. Thus, the effects similar to the first embodiment are obtained. In the present embodiment, in view of the influence of variations of individual products of each circuit and the sensor 2, the influence is removed.

In the present embodiment, the offset voltage Voffset is added to the initial voltage V1 in the initial state in the positive direction. Alternatively, the offset voltage Voffset may be subtracted from the initial voltage V1. The offset volateg Voffset may be set appropriately in view of variations of temperature dependency of the sensor 2. Thus, the control device 3 can flexibly execute the functions in accordance with the element characteristics of the sensor 2 or the like.

Other Embodiments

In the above embodiments, the control device 3 includes the A/D converting unit 14 so that the digital values stored in the memories 15, 16 are compared with each other. Alternatively, the function of the voltage comparison unit 17 may be provided by a voltage comparison device such as a comparator, so that the inter-terminal voltage of the sensor 2 is compared as an analog signal.

In the above case, a D/A converter may be arranged on a latter step of the A/D converting unit 14. The output analog signal from the D/A converter is compared by a comparator. Therefore, the control device processes the signal in an analog manner. Alternatively, the voltage between the terminals 3a, 3b of the sensor 2 may be input into the comparator as an analog signal, and the comparator compares the input signal with the analog voltage corresponding to the stored voltage in the pre-sweeping voltage memory 15.

The control circuit 4 provides the A/D converting unit 14 integrally with using the micro computer. Alternatively, the A/D converting unit 14 may be an external device attached to the micro computer.

While the present disclosure has been described with reference to embodiments thereof, it is to be understood that the disclosure is not limited to the embodiments and constructions. The present disclosure is intended to cover various modification and equivalent arrangements. In addition, while the various combinations and configurations, other combinations and configurations, including more, less or only a single element, are also within the spirit and scope of the present disclosure.

What is claimed is:

1. A control device for controlling an oxygen concentration sensor comprising:
    a voltage sweeping unit for applying a voltage to the oxygen concentration sensor for a predetermined time interval during an impedance detection process, in which information about an exhaust gas air and fuel ratio is obtained according to a terminal voltage of the oxygen concentration sensor;
    a pre-sweeping voltage memory for storing an initial terminal voltage, which is the terminal voltage of the oxygen concentration sensor just before the voltage sweeping unit applies the voltage to the oxygen concentration sensor;
    an impedance detection unit for detecting an element impedance in accordance with the voltage applied by the voltage sweeping unit;
    a voltage returning unit for returning the terminal voltage of the oxygen concentration sensor to the initial terminal voltage after the predetermined time interval has elapsed from when the voltage sweeping unit applies the voltage to the oxygen concentration sensor;

a monitoring unit for monitoring the terminal voltage of the oxygen concentration sensor after the voltage returning unit starts returning the terminal voltage of the oxygen concentration sensor to the initial terminal voltage;

a determination unit for comparing a monitored terminal voltage of the oxygen concentration sensor with the initial terminal voltage stored in the pre-sweeping voltage memory, and for determining when the monitored terminal voltage reaches the initial terminal voltage; and a stop unit for stopping a returning operation of the voltage returning unit when the determination unit determines that the monitored terminal voltage reaches the initial terminal voltage.

2. A control device for controlling an oxygen concentration sensor comprising:

a voltage sweeping unit for applying a voltage to the oxygen concentration sensor for a predetermined time interval during an impedance detection process, in which information about an exhaust gas air and fuel ratio is obtained according to a terminal voltage of the oxygen concentration sensor;

a pre-sweeping voltage memory for storing an initial terminal voltage, which is the terminal voltage of the oxygen concentration sensor just before the voltage sweeping unit applies the voltage to the oxygen concentration sensor;

an impedance detection unit for detecting an element impedance in accordance with the voltage applied by the voltage sweeping unit;

a voltage returning unit for returning the terminal voltage of the oxygen concentration sensor to the initial terminal voltage after the predetermined time interval has elapsed from when the voltage sweeping unit applies the voltage to the oxygen concentration sensor;

a monitoring unit for monitoring the terminal voltage of the oxygen concentration sensor after the voltage returning unit starts returning the terminal voltage of the oxygen concentration sensor to the initial terminal voltage;

a determination unit for comparing a monitored terminal voltage of the oxygen concentration sensor with a certain voltage, which is calculated by adding an offset voltage to, or subtracting the offset voltage from, the initial terminal voltage stored in the pre-sweeping voltage memory, and for determining when the monitored terminal voltage reaches the certain voltage; and a stop unit for stopping a returning operation of the voltage returning unit when the determination unit determines that the monitored terminal voltage reaches the certain terminal voltage.

* * * * *